(12) United States Patent
Gunasekera et al.

(10) Patent No.: US 7,053,118 B1
(45) Date of Patent: May 30, 2006

(54) LACTONE COMPOUNDS AND METHODS OF USE

(75) Inventors: Sarath P. Gunasekera, Vero Beach, FL (US); Ross E. Longley, Tallahassee, FL (US); Amy E. Wright, Fort Pierce, FL (US); John K. Reed, Ft. Pierce, FL (US)

(73) Assignee: Harbor Branch Oceanographic Institution, Inc., Ft Pierce, FL (US)

( * ) Notice: Subject to any disclaimer, the term of this patent is extended or adjusted under 35 U.S.C. 154(b) by 498 days.

(21) Appl. No.: 10/382,369

(22) Filed: Mar. 6, 2003

(51) Int. Cl.
- *A01N 43/08* (2006.01)
- *A61K 31/34* (2006.01)
- *C07D 307/02* (2006.01)
- *C07D 407/00* (2006.01)

(52) U.S. Cl. ................ 514/473; 549/295
(58) Field of Classification Search ........... 514/473; 549/295

See application file for complete search history.

(56) References Cited

U.S. PATENT DOCUMENTS

| | | |
|---|---|---|
| 4,206,221 A | 6/1980 | Miller et al. |
| 4,548,814 A | 10/1985 | Rinehart, Jr. et al. |
| 4,729,996 A | 3/1988 | Wright et al. |
| 4,737,510 A | 4/1988 | Rinehart, Jr. et al. |
| 4,808,590 A | 2/1989 | Higa et al. |
| 4,960,790 A | 10/1990 | Stella et al. |
| 5,157,049 A | 10/1992 | Haugwitz et al. |
| 5,789,605 A | 8/1998 | Smith et al. |

FOREIGN PATENT DOCUMENTS

WO  WO 9824429  6/1998

OTHER PUBLICATIONS

Faulkner, D.J. "Marine Natural Products" *Natural Products Reports* 1998, vol. 15, pp. 113-158.

Fuchs, D.A. Johnson, R.K. "Cytologic evidence that taxol, an antineoplastic agent from *Taxus brevifolia*, acts as a mitotic spindle poison" *Cancer Treat. Rep.* 1978, vol. 62, pp. 1219-1222.

Gunasekera, S.P. et al. "Discodermolide: A new bioactive polyhydroxy lactone from the marine sponge *Discodermia dissolute*" *J. Org. Chem.* 1990, vol. 55, pp. 4912-4915 [correction *J. Org. Chem.* 1991, vol. 56, p. 1346.]

Kowalski et al. "The microtubule-stabilizing agent discodermolide competitively inhibits the binding of paclitaxel (Taxol) to tubulin polymers, enhances tubulin nucleation reactions more potently than paclitaxel, and inhibits the growth of paclitaxel-resistant cells" *Mol. Pharmacol.* 1997, vol. 52, pp. 613-622.

Minale, L. et al. "Natural products from porifera" *Fortschr. Chem. Org. Naturst.* 1976, vol. 33, pp. 1-72.

Rowinski, E.K., Donehower, R.C. "Paclitaxel (Taxol)" *N. Engl. J. Med.* 1995, vol. 332, pp. 1004-1014.

Scheuer, P.J. (ed.) *Marine Natural Products, Chemical and Biological Perspectives*, Academic Press, New York, 1978-1983, vol. I-V.

Schiff, P.B et al. "Promotion of microtubule assembly in vitro by taxol" *Nature* 1979, vol. 22, pp. 665-667.

Ter Haar et al. "Discodermolide, a cytotoxic marine agent that stabilizes microtubules more potently than taxol" *Biochemistry* 1996, vol. 35, pp. 243-250.

Uemura, D. et al. "Norhalichondrin A: An Antitumor Polyether Macrolide from a Marine Sponge" *J. Am. Chem. Soc.* 1985, vol. 107, pp. 4796-4798.

*Primary Examiner*—Shengjun Wang
*Assistant Examiner*—Yong S. Chong
(74) *Attorney, Agent, or Firm*—Saliwanchik, Lloyd & Saliwanchik

(57) ABSTRACT

The subject invention provides novel compositions of biologically active compounds which can advantageously be used for inhibiting pathological cellular proliferation. The compounds of the subject invention have utility for use in the treatment of cancer, including tumors.

10 Claims, No Drawings

LACTONE COMPOUNDS AND METHODS OF USE

FIELD OF THE INVENTION

This invention relates to lactone compounds and compositions which have useful therapeutic properties. More particularly, the invention provides compounds having antitumor activities, pharmaceutical compositions comprising such compounds, methods for the preparation of the compounds, and compositions and methods of their use.

BACKGROUND OF INVENTION

Various tumor and cancer related diseases afflict man and animals. The term "tumor" refers to abnormal masses of new tissue growth which is discordant with the economy of the tissue of origin or of the host's body as a whole. Tumors inflict mammals and man with a variety of disorders and conditions, including various forms of cancer. The seriousness of cancer is well known, e.g. cancer is second only to heart and vascular diseases as a cause of death in man. Tumors are common in a variety of mammals, and the prevention and control of the growth and regression of tumors in mammals is important to man.

Considerable research and resources have been devoted to oncology and antitumor measures, including chemotherapy. While certain methods and chemical compositions have been developed which aid in inhibiting, remitting, or controlling the growth of tumors and other forms of cancer, further antitumor methods and chemical compositions are needed.

It has been found that some natural products and organisms are potential sources for chemical molecules having useful biological activities. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge *Theonella* sp.; and U.S. Pat. No. 4,737,510 discloses compounds, having antiviral and antibacterial properties, isolated from the Caribbean sponge *Agelas coniferin*.

A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1998) *Natural Products Reports* 15:113–158; and Gunasekera, S. P., M. Gunasekera, R. E. Longley and G. K. Schulte (1990) "Discodermolide: A new bioactive polyhydroxy lactone from the marine sponge *Discodermia dissoluta*" *J. Org. Chem.*, 55:4912–4915 [correction (1991) *J. Org. Chem.* 56:1346]. U.S. Pat. No. 4,808,590 discloses compounds, having antiviral, antitumor, and antifungal properties, isolated from the marine sponge *Theonella* sp. (International Patent Application No. WO 9824429; Kowalski, R. J., P. Giannakakou, S. P. Gunasekera et al. (1997) *Mol. Pharmacol* 52:613–622; ter Haar, E., R. J. Kowalski, E. Hamel et al. (1996) *Biochemistry* 35:243–250; Stafford, J. A. and M. M. Mehrotra (1995) *Chemtract: Org. Chem.* 8:41–47; and U.S. Pat. No. 5,789,605.

BRIEF SUMMARY

The subject invention provides novel lactone compounds having advantageous biological activities. Specifically, in one embodiment, the lactone compounds and compositions of the subject invention can be used in the treatment of an animal (including humans) hosting cancer cells, including, for example, inhibiting the growth of tumor cells in a mammalian host. More particularly, the subject compounds can be used for inhibiting in a human the growth of tumor cells, including cancer cells of the pancreas, breast, colon, CNS, ovarian, renal, prostrate, lung, leukemia and melanoma cells. Specifically exemplified is plakolide A and its analogs.

Also provided according to the subject invention are compositions containing the biologically active lactone compounds, as well as methods for the preparation and use of the compounds and compositions.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE

The subject invention pertains, in part, to novel lactone compounds and the use of these compounds to prevent pathological cellular proliferation. In a specific embodiment, the subject invention pertains to a novel compound known as plakolide A, as well as its analogs. The compounds of the subject invention can be formulated into pharmaceutical compositions and can be used to treat tumors and others forms of pathological cellular proliferation.

The compounds described are useful as antitumor agents. The compositions and methods of the subject invention can be used in the treatment of an animal (including humans) hosting cancer cells, including, for example, inhibiting the growth of tumor cells in a mammalian host. More particularly, the subject compounds can be used for inhibiting in a human the growth of tumor cells, including cancer cells of the pancreas, breast, colon, CNS, ovarian, renal, prostate, lung, leukemia and melanoma cells.

The present invention, utilizing sponges as a source material, provides the art with new biologically active compounds and new pharmaceutical compositions useful as antitumor agents. The present invention has added to the arsenal of pharmaceutical compounds by the discovery of novel compounds isolatable from extracts of marine sponges of the family Plakinidae.

Collection and Taxonomy. The sponge sample was collected by scuba, from the wall of a cave at a depth of 3.3 m, near La Palma, Canary Islands (Latitude 28° 41.75' N; Longitude 17° 58.00' W). This sponge most closely fits the genus *Plakortis* Schulz, 1880 (class Demospongia, order Homosclerophorida, family Plakinidae), but can not be ascribed to a known species at this time. The specimen was encrusting on the rock surface of a cave wall. It was ~15 cm diameter and ~1 cm thick, with a smooth ectosome. The color in situ was light brown. The spicule skeleton consists of diods and occasional triods. A museum voucher specimen preserved in EtOH has been deposited at the Harbor Branch Oceanographic Museum, catalog number 003:00976 and is available for taxonomic evaluation.

Extraction and Isolation. The sponge was extracted in EtOH (3×300 mL) and concentrated to give 9.3 g of the EtOH extract. The EtOH extract was partitioned between EtOAc and $H_2O$. The EtOAc-soluble fraction (1.8 g) was chromatographed on a column of Si gel (230–400 mesh) using a $CH_2Cl_2$-MeOH step gradient, and the fractions were monitored for cytotoxic activity. The cytotoxic fraction that eluted with $CH_2Cl_2$ was rechromatographed over Si gel using a hexane-$CH_2Cl_2$ step gradient and the fractions were monitored again for cytotoxic activity. The active fraction (0.037 g) that eluted with 25% hexane-$CH_2Cl_2$ was further purified by HPLC (Phenomenex, $SiO_2$, 5 µm, 250×10 mm) with hexane-EtOAc gradient (95:5 to 80:20 in 16 min, 3 mL/min) gave plakolide A (1) as a colorless gum (3.4 mg, 0.015% of wet wt).

Compounds useful according to the subject invention can be isolated by various fractionation and chromatographic techniques from the extracts obtained as disclosed herein. Preferred isolation procedures include various chromatography techniques, such as countercurrent chromatography, with suitable columns including multi-layer planetary coil columns. A variety of solvents are available for use as single or mixed eluents, such as tetrahydrofuran, methanol, ethyl acetate, acetonitrile, n-propanol, n-butanol, water, and equivalent solvents. Further purifications using such procedures may also be carried out on the recovered extractions. Preferred isolation techniques for further purifications include chromatographic operations such as high-pressure liquid chromatography (HPLC) with suitable columns and suitable solvents.

Plakolide A, is an α-exomethylene-γ-disubstituted-γ-lactone. These chiral unusually functionalized γ-lactones are uncommon among natural products and this is the first report from a marine organism. The αβ and γδ trans diene dodecane side chain that is attached to the γ position of the lactone ring is accountable for the liphophilicity of the compound. The unusual substitution pattern in the γ-lactone ring may be contributing to the biological activity of the compound.

Included within the scope of the subject invention are analogs (equivalents) of the compounds. As used in this application, the term "analogs" refers to compounds which are substantially the same as another compound but which may have been modified by, for example, adding side groups. Salts are also within the scope of the present invention. Analogs of the exemplified compounds can be readily prepared using commonly known, standard reactions. These standard reactions include, but are not limited to, hydrogenation, methylation, acetylation, and acidification reactions.

Thus, the subject invention pertains, in part, to plakolide A (1) having the following structure and characteristics:

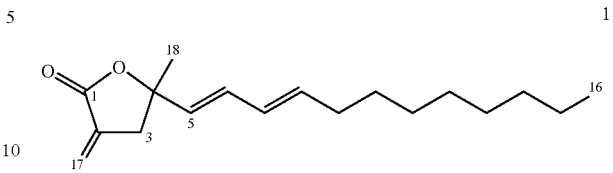

Plakolide A (1): $[\alpha]^{24}_D$ −31° (c 0.1, $CH_3OH$); UV (MeOH) $\lambda_{max}$ 208 (logε4.36), 230 (4.47) nm; IR (NaCl disc) $\nu_{max}$ 2934, 2858, 1768, 1457, 1380, 1269, 1208, 1108, 1051, 993, 941 $cm^{-1}$; $^1H$ NMR (500 MHz, $CDCl_3$ referenced at δ 7.24) δ 6.21 (1H, dd, J=15.4, 10.4 Hz, H-6), 6.20 (1H, t, J=2.4 Hz, H-17), 5.97 (1H, dd, J=15.0, 10.4 Hz, H-7), 5.73 (1H, dt, J=15.0, 6.9 Hz, H-8), 5.58 (1H, d, J=15.4 Hz, H-5), 5.57 (1H, t, J=2.4 Hz, H-17), 2.89 (1H, dt, J=16.5, 2.4 Hz, H-3), ), 2.77 (1H, dt, J=16.5, 2.4 Hz, H-3), 2.05 (2H, dt, J=7.2, 6.9 Hz, H-9), 1.50 (3H, s, H-18), 1.33 (2H, m, H-10), 1.15 (10H, m, H11–H15), 0.85 (3H, t, J=7.2 Hz, H-16); $^{13}C$ NMR (125.7 MHz, $CDCl_3$ referenced at δ 77.0) δ 169.8 (s, C-1), 137.4 (d, C-8), 135.4 (s, C-2), 132.2 (d, C-5), 129.7 (d, C-6), 128.7 (d, C-7), 122.2 (t, C-17), 82.4 (s, C-4), 40.8 (t, C-3), 32.7 (t, C-9), 31.9 (t, C-14), 29.4, 29.3, 29.2, 29.1 (t, C-10–C13), 27.1 (q, C-18), 22.7 (t, C-15), 14.1 (q, C-16); HRFABMS (thioglycerol) m/z 277.2116, Δ 5 mmu for $C_{18}H_{29}O_2$ $[M+H]^+$.

Additional preferred embodiments include 5,7-tetrahydroplakolide A (2) and 5,7, (2–17)-hexahydroplakolide A (3)

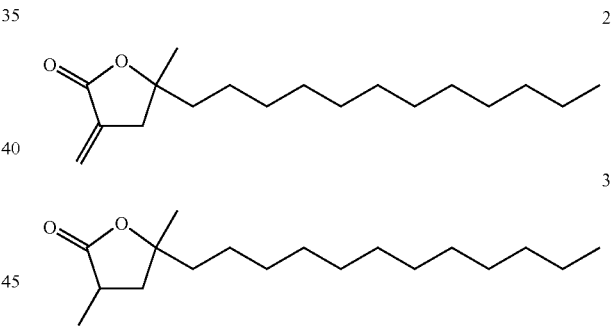

Further preferred embodiments include:

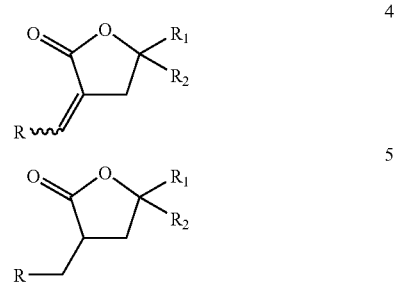

R=H and $R_1$, $R_2$=combination of $C_1$ to $C_{12}$

The chiral compounds of the subject invention can be administered as a racemic mixture or in their single enantiomer forms. For the administration of a single enantiomer, the isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

As described herein, the invention also comprises the use of the new compounds of the subject invention for inhibiting unwanted cellular proliferation and, in a preferred embodiment, for the inhibition of tumor growth. Thus, one aspect of the subject invention is a method for the antitumor treatment of a human in need of such treatment, i.e., a human hosting cancer cells, including breast, colon, or lung tumor cells, leukemia cells, CNS cancer cell lines, melanoma cell lines, ovarian cancer cell lines, renal cancer cell lines, and prostate cancer cell lines.

In accordance with the invention, methods for inhibiting tumors in a host comprise contacting tumor cells with an effective amount of the new pharmaceutical compositions of the invention. The tumor cells inhibited by the invention are those which are susceptible to the subject compounds described herein or compositions comprising those compounds.

A more complete understanding of the invention can be obtained by reference to preferred embodiments of the invention which are illustrated by the following specific examples of compounds, compositions, and methods of the invention. It will be apparent to those skilled in the art that the examples involve use of materials and reagents that are commercially available from known sources, e.g., chemical supply houses, so no details are given respecting them.

Following are examples which illustrate procedures for practicing the invention. These examples should not be construed as limiting. All percentages are by weight and all solvent mixture proportions are by volume unless otherwise noted.

EXAMPLE 1

Antitumor Activity

Extracts and compounds were analyzed as to their effects on proliferation of A549 human adenocarcinoma, PANC-1 human pancreatic and P388 murine leukemia cell lines. P388 cells were obtained from Dr. R. Camalier, National Cancer Institute, Bethesda, Md., and A549 and PANC-1 cells were obtained from American Type Culture Collection, Rockville, Md. All cell lines were maintained in Roswell Park Memorial Institute (RPMI) medium 1640 supplemented with 10% fetal bovine serum. All cell lines are cultured in plastic tissue culture flasks and kept in an incubator at 37° C. in humidified air containing 5% $CO_2$. Prior to testing, antibiotic-free stock cultures of each of the cell lines were subcultured to $10^6$ cells/ml by dilution in fresh growth medium at 2 to 3 day intervals.

To assess the antiproliferative effects of extracts and compounds against the P388 cell line, 200 μl cultures (96-well tissue culture plates, Nunc, Denmark) are established at $1\times10^5$ cells/ml in drug-free medium or medium containing the test agent at 10.0, 1.0, 0.10 and 0.010 μg/ml. Solvent for all dilutions ethanol. All experimental cultures are initiated in medium containing Gentamycin sulfate (50 μg/ml; Schering Corporation, Kenilworth, N.J.). After 48-h exposures, P388 cells are enumerated using 3-[4,5-dimethylthiazol-2-yl]-2,5-diphenyltetrazolium bromide (MTT) as described below (M. C. Alley, et al., Cancer Res. 48:589, 1988).

Similar procedures are utilized for A549 and PANC-1 cells which require an additional 48 hr exposure prior to MTT addition. Results are expressed as percent inhibition compared to the negative (no drug) control. Positive drug controls are included to monitor drug sensitivity of each of the cell lines. These include varying dilutions of 5-fluorouracil and adriamycin.

To quantitate the effects of pure compounds on cell proliferation and resulting $IC_{50}$ values, 75 μl of warm growth media containing 5 mg/ml MTT is added to each well, cultures returned to the incubator, and left undisturbed for 90 minutes. To spectrophotometrically quantitate formation of reduced formazan, plates are centrifuged (900×g, 5 minutes), culture fluids removed by aspiration, and 200 μl of acidified isopropanol (2 ml concentrated HCl/liter isopropanol) added per well. The absorbance of the resulting solutions is measured at 570 nm with a plate reader (TECAN Spectra II Plate Reader, TECAN U.S., Research Triangle Park, N.C.). The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp. 316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination. Table 1 summarizes the activities determined for plakolide A.

TABLE 1

| Assay | Activity ($IC_{50}$ μg/ml) |
| --- | --- |
| P-388 | 1.09 μg/ml |
| A549 | 5.0 μg/ml |
| PANC-1 | 3.78 μg/ml |

EXAMPLE 2

Uses, Formulations, and Administrations

Therapeutic and prophylactic application of the lactone compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes.

In one embodiment, the compounds of the subject invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for inhibiting the growth of cancer cells, said method comprising administering to said cells an effective amount of a compound, wherein said compound has the structure shown below:

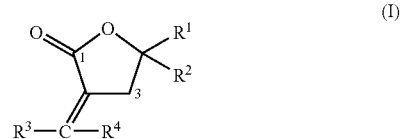

wherein
$R^1$ is $CH_3$, $R^2$ is trans-($\alpha\beta$, $\gamma\delta$)-dodecadiene and $R^3$ and $R^4$ are hydrogen and wherein said cancer cells are selected from the group consisting of leukemia, lung cancer, and pancreatic cancer.

2. The method, according to claim 1, wherein said compound is administered as a racemic mixture.

3. The method, according to claim 1, wherein said compound is administered in a single enantiomer form.

4. The method, according to claim 1, wherein said compound is administered as a pharmaceutical composition comprising an acceptable carrier.

5. An isolated compound, wherein said compound has the structure shown below:

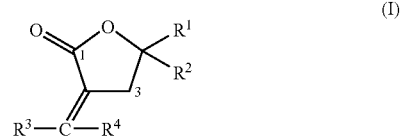

wherein $R^1$ is $CH_3$, $R^2$ trans-($\alpha\beta$, $\gamma\delta$)-dodecadiene and $R^3$ and $R^4$ are hydrogen.

6. The compound, according to claim 5, wherein said compound is a racemic mixture.

7. The compound, according to claim 5, wherein said compound is in a single enantiomer form.

8. A pharmaceutical composition, wherein said composition comprises a compound having the structure shown below:

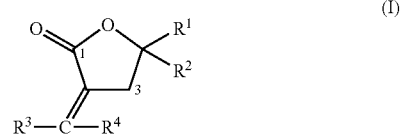

wherein
$R_1$ is $CH_3$, $R^2$ trans-($\alpha\beta$, $\gamma\delta$)-dodecadiene and $R^3$ and $R^4$ are hydrogen.

9. The pharmaceutical composition, according to claim 8, wherein said compound is administered as a racemic mixture.

10. The pharmaceutical composition, according to claim 8, wherein said compound is administered in a single enantiomer form.

* * * * *